(12) United States Patent
Jensen et al.

(10) Patent No.: US 8,099,170 B2
(45) Date of Patent: Jan. 17, 2012

(54) ELECTRICAL STIMULATION BASED ON PHASE RESPONSE MAPPING

(75) Inventors: Steven L. Jensen, Andover, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 55 days.

(21) Appl. No.: 12/727,889

(22) Filed: Mar. 19, 2010

(65) Prior Publication Data

US 2011/0230936 A1     Sep. 22, 2011

(51) Int. Cl.
*A61N 1/00*     (2006.01)
(52) U.S. Cl. .......................................... 607/62
(58) Field of Classification Search ........... 607/62
See application file for complete search history.

(56) References Cited

U.S. PATENT DOCUMENTS

| | | | |
|---|---|---|---|
| 6,304,775 B1 * | 10/2001 | Iasemidis et al. ............ | 600/544 |
| 7,353,064 B2 | 4/2008 | Gliner et al. | |
| 7,437,196 B2 | 10/2008 | Wyler et al. | |
| 7,483,747 B2 | 1/2009 | Gliner et al. | |
| 2003/0149457 A1 | 8/2003 | Tcheng et al. | |

FOREIGN PATENT DOCUMENTS

| | | |
|---|---|---|
| EP | 1985230 A1 | 10/2008 |
| WO | 2008109508 A2 | 9/2008 |

OTHER PUBLICATIONS

Tateno et al., "Phase Resetting Curves and Oscillatory Stability in Interneurons of Rat Somatosensory Cortex," Biophysical Journal, vol. 92, Jan. 2007, 13 pages.

Hauptmann et al., "Cumulative and after-effects of short and weak coordinated reset stimulation: a modeling study," Journal of Neural Engineering, vol. 6, Jan. 2009, 13 pages.

Tass, "Desynchronization of brain rhythms with soft phase-resetting techniques," Biological Cybernetics, vol. 87, Feb. 2002, 14 pages.

Zhai et al., "Desynchronization of coupled electrochemical oscillators with pulse stimulations," Physical Review E, vol. 71, Jun. 2005, 4 pages.

Hauptmann et al., "Effectively desynchronizing deep brain stimulation based on a coordinated delayed feedback stimulation via several sites: a computational study," Biological Cybernetics, vol. 93, Sep. 2005, 8 pages.

Tass, "A model of desynchronizing deep brain stimulation with a demand-controlled coordinated reset of neural subpopulations," Biological Cybernetics, vol. 89, Jul. 2003, 8 pages.

(Continued)

*Primary Examiner* — George Manuel
(74) *Attorney, Agent, or Firm* — Shumaker & Sieffert, P.A.

(57) ABSTRACT

This disclosure describes techniques for delivering electrical stimulation at one or more phases relative to an ongoing oscillating signal in a patient, and then mapping the response to the oscillating signal. The techniques may reduce or eliminate the oscillating signal. In one example, the disclosure is directed to a method that includes delivering a set of first electrical stimulation at a plurality of phases relative to an oscillating signal, measuring a response in the oscillating signal to the set of first electrical stimulation after delivering electrical stimulation at each respective phase of the plurality of phases, determining a phase at which to deliver second electrical stimulation based on the measured responses, and delivering the second electrical stimulation to the patient at the determined phase to produce a therapeutic effect.

25 Claims, 8 Drawing Sheets

OTHER PUBLICATIONS

Tass, "Desynchronizing double-pulse phase resetting and application to deep brain stimulation," Biological Cybernetics, vol. 85, Apr. 2001, 12 pages.

Hauptmann et al., "Desynchronizing the abnormally synchronized neural activity in the subthalamic nucleus: a modeling study," Expert Review Medical Devices, Sep. 2007, 18 pages.

Tass, "Effective desynchronization with bipolar double-pulse stimulation," Physical Review E, vol. 66, Sep. 2002, 9 pages.

Tass, "Effective desynchronization with a resetting pulse train followed by a single pulse," Europhysics Letters, vol. 55(2), May 2001, 7 pages.

Popovych et al., "Effective Desynchronization by Nonlinear Delayed Feedback," The American Physical Society, Apr. 2005, 4 pages.

Tass et al., "Obsessive-Compulsive Disorder: Development of Demand-Controlled Deep Brain Stimulation with Methods from Stochastic Phase Resetting," Neuropsychopharmacology, Jul. 2003, 8 pages.

Neiman, "Response clustering in transient stochastic synchronization and desynchronization of coupled neuronal bursters," Physical Review E, vol. 76, Aug. 2007, 10 pages.

Krachkovskyi et al.,"Stimulus-locked responses of two phase oscillators coupled with delayed feedback," Physical Review E, vol. 73, Jun. 2006, 18 pages.

Tass et al., "Therapeutic modulation of synaptic connectivity with desynchronizing brain stimulation," International Journal of Psychophysiology, vol. 64, Apr. 2007, 9 pages.

Hauptmann et al., "Therapeutic rewiring by means of desynchronizing brain stimulation," Elsevier, Biosystems, vol. 89, May-Jun. 2007, 9 pages www.sciencedirect.com.

Barnikol et al., "Tremor entrainment by patterned low-frequency stimulation," Philosophical Transactions of The Royal Society A, Mathematical, Physical & Engineering Sciences, Oct. 2009, 30 pages.

Tass et al., "Long-lasting desynchronization in rat hippocampal slice induced by coordinated reset stimulation," Physical Review E, vol. 80, Jul. 2009, 4 pages.

Tass et al., "Long-term anti-kindling effects of desynchronizing brain stimulation: a theoretical study," Biological Cybernetics, vol. 94, Jan. 2006, 9 pages.

Popovych et al., "Impact of Nonlinear Delayed Feedback on Synchronized Oscillators," Journal of Biological Physics, vol. 34, May 2008, 13 pages.

Majtanik et al., "Desynchronization in Networks of Globally Coupled Neurons with Dendritic Dynamics," Journal of Biological Physics, vol. 32, Nov. 2006, 27 pages.

Popovych et al., "Control of Neuronal synchrony by nonlinear delayed feedback," Biological Cybernetics, vol. 95, Apr. 2006, 18 pages.

Omel'chenko et al., "Chimera States: The Natural Link Between Coherence and Incoherence," The American Physical Society, Feb. 2008, 4 pages.

Hauptmann et al., "Control of spatially patterned synchrony with multisite delayed feedback," Physical Review E, vol. 76, Dec. 2007, 6 pages.

Vlachos et al., "Discovering Similar Multidimensional Trajectories," Proceedings of the 18th International Conference on Data Engineering, Feb. 2002, 12 pages.

Patent application entitled Medical Method and Device for Monitoring a Neural Brain Network, U.S. Appl. No. 12/826,172, filed Jun. 29, 2010, Wu et al.

Notification of Transmittal of the International Search Report and the Written Opinion of the International Searching Authority for corresponding patent application No. PCT/US2011/028533, dated Aug. 24, 2011, 12 pages.

* cited by examiner

ELECTRICAL STIMULATION BASED ON PHASE RESPONSE MAPPING

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) by a medical device to one or more sites in a patient, such as a brain, spinal cord, leg muscle or arm muscle, in a patient may help alleviate, and in some cases, eliminate symptoms associated with movement disorders.

SUMMARY

In general, the disclosure is directed toward techniques for delivering electrical stimulation at one or more phases relative to an ongoing oscillating signal in the patient, mapping the phase dependent or independent responses of the oscillating signal to the stimulation, and then delivering subsequent electrical stimulation therapy based on the characterized responsiveness. The electrical stimulation may include, for example, single pulses, pulse trains, or continuous waveforms. In some examples, delivering electrical stimulation at a specific phase determined from the mapped responses may induce a phase reset of the oscillating signal, e.g., an advance or a delay in the oscillating signal and/or a decrease in the amplitude of the oscillating signal, and thereby improve or maintain the patient's movements and/or cognitive states.

In one example, the disclosure is directed to a method comprising delivering a set of first electrical stimulation at a plurality of phases relative to an oscillating signal, after delivering the set of first electrical stimulation at each respective phase of the plurality of phases, measuring a response in the oscillating signal to the set of first electrical stimulation, determining a phase at which to deliver second electrical stimulation based on the measured responses, delivering the second electrical stimulation to the patient at the determined phase to produce a therapeutic effect.

In another example, the disclosure is directed to a device comprising an implantable housing, one or more leads coupled to the housing, one or more electrodes carried by the one or more leads, and a processor. The processor is configured to control delivery of a set of first electrical stimulation at a plurality of phases relative to an oscillating signal, after delivery of the set of first electrical stimulation at each respective phase of the plurality of phases, measure a response in the oscillating signal to the first electrical stimulation, determine a phase at which to deliver second electrical stimulation based on the measured responses, and control delivery of the second electrical stimulation to the patient at the determined phase to produce a therapeutic effect.

In another example, the disclosure is directed to a computer-readable storage medium comprising instructions that, when executed by a processor, cause the processor to control delivery of a set of first electrical stimulation at a plurality of phases relative to an oscillating signal, after delivery of the set of first electrical stimulation at each respective phase of the plurality of phases, measure a response in the oscillating signal to the set of first electrical stimulation, determine a phase at which to deliver second electrical stimulation based on the measured responses, and control delivery of the second electrical stimulation to the patient at the determined phase.

In another example, the disclosure is directed to a device comprising means for delivering first electrical stimulation at a plurality of phases relative to an oscillating signal, means for measuring a response in the oscillating signal to the set of first electrical stimulation after delivering the first electrical stimulation at each respective phase of the plurality of phases, means for determining a phase at which to deliver second electrical stimulation based on the measured responses, and means for delivering the second electrical stimulation to the patient at the determined phase to produce a therapeutic effect.

The details of one or more aspects of the disclosure are set forth in the accompanying drawings and the description below. Other features, objects, and advantages of the invention will be apparent from the description and drawings, and from the claims.

DETAILED DESCRIPTION

Figure 1:
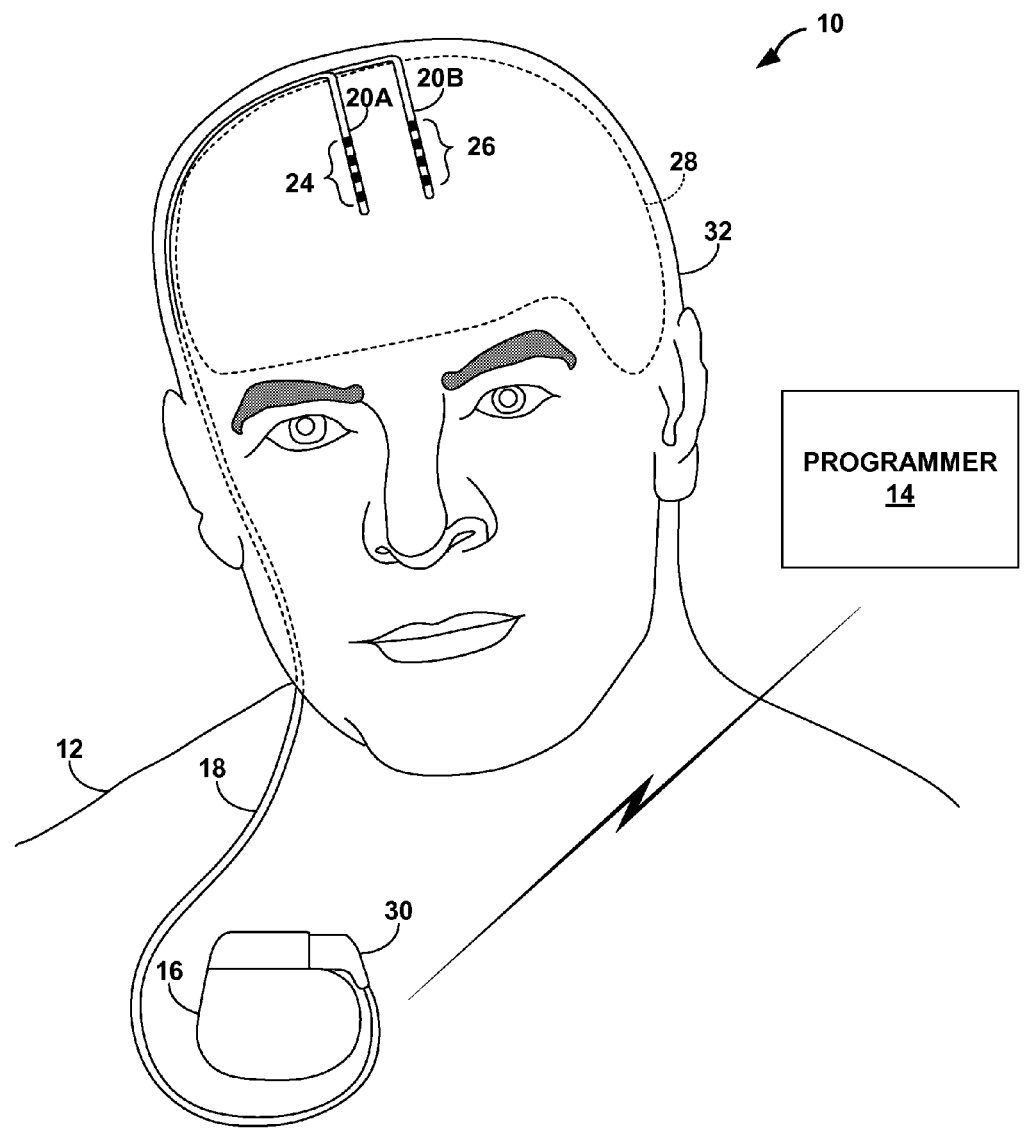
FIG. 1 is a conceptual diagram illustrating an example deep brain stimulation (DBS) system that may be used to implement the techniques of this disclosure.

This disclosure describes techniques for reducing, eliminating or otherwise modifying oscillating signals in the brain. Brain rhythms may be recorded, for example, in the form of local field potentials (LFP) and/or electroencephalogram (EEG) or electrocorticogram (ECoG) signals sensed by an implantable or external medical device. Brain LFP, EEG, or ECoG rhythms may be associated with pathologies in various neurological and psychological disorders. Using the techniques of this disclosure, these brain rhythms may be reduced or eliminated using electrical stimulation. In many physiological systems that oscillate, a single specific electrical stimulus or several stimuli will induce phase resets of the rhythmicity, alter the period and/or amplitude of the rhythmicity for extended time periods, or even eliminate rhythmicity. Precise timing of the stimulus onset, duration, and amplitude relative to a specific rhythmicity may achieve a rapid reduction in the amplitude of an oscillating system or even eliminate the oscillating rhythm.

Using the techniques of this disclosure, the precise timing for delivery of electrical stimulation therapy, as well as stimulation parameters that may be needed for rhythm control, may be determined. Test pulses can be delivered to an oscillating system at random phases or specific phases relative to the ongoing oscillation, and the phase of each test pulse relative to an ongoing oscillating signal in the oscillating system may be determined. Additionally, the phase resetting responses of the oscillation to each test pulse may be determined and recorded in order to generate a phase response map that characterizes the responses of the oscillating signal to electrical stimulation. Based on the generated phase response map, the precise timing and specific parameter sets for delivery of a single stimulus, e.g., a single therapeutic stimulation pulse, or multiple therapeutic stimulation pulses, e.g., a train of therapeutic stimulation pulses, can be determined for a specific patient and for a specific oscillating signal.

Brief electrical stimulation test pulses may be delivered to the patient and the resulting changes in phase and amplitude of the oscillating signal, or rhythm, may be quantified and recorded for each stimulation pulse. Stimulation amplitude (current or voltage), duration, and phase of test pulse delivery may each be adjusted, and their effects on the ongoing oscillating signal may be recorded. Once a complete phase response map is generated, the map may be used to calculate the stimulation parameters that may reduce or eliminate the oscillating signal. For example, the timing of stimulus delivery and its amplitude may be determined based on the phase response map. If the oscillating signal is reduced in amplitude or altered in frequency by the stimulus delivery, a device and/or a system may determine the stimulation parameters and timing that caused the efficacy observed in the oscillating signal in terms of reducing or eliminating the signal, or may initiate generation of a phase response map of the new oscillating signal and determine the parameters required for subsequent electrical stimulation for further reduction or elimination.

FIG. 1 is a conceptual diagram illustrating an example deep brain stimulation (DBS) system that may be used to implement the techniques of this disclosure. In FIG. 1, example therapy system 10 may deliver electrical stimulation therapy to control a patient condition, such as a movement disorder or a neurodegenerative impairment of patient 12. Patient 12 ordinarily will be a human patient. In some cases, however, therapy system 10 may be applied to other mammalian or non-mammalian non-human patients. While movement disorders and neurodegenerative impairment are primarily referred to in this disclosure, in other examples, therapy system 10 may provide therapy to manage symptoms of other patient conditions, such as, but not limited to, seizure disorders or psychological disorders.

A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions. Although movement disorders are primarily referred to throughout the remainder of the disclosure, the therapy systems and methods described in this disclosure are also useful for controlling symptoms of other conditions, such as neurodegenerative impairment.

In the example of FIG. 1, therapy system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B are positioned to deliver electrical stimulation to a tissue site within brain 28, such as a deep brain site under the dura mater of brain 28 of patient 12. In some examples, delivery of stimulation to one or more regions of brain 28, such as the subthalmic nucleus, globus pallidus internus or thalamus, may be an effective treatment to manage movement disorders, such as Parkinson's disease or essential tremor, as well to manage chronic pain, depression, epilepsy, migraines, and Alzheimer's disease, for example.

IMD 16 includes a therapy module that includes a stimulation generator that generates and delivers electrical stimulation therapy to patient 12 via a subset of electrodes 24, 26 of leads 20A and 20B, respectively. The subset of electrodes 24, 26 that are used to deliver electrical stimulation to patient 12, and, in some cases, the polarity of the subset of electrodes 24, 26, may be referred to as a stimulation electrode combination. It should be noted that leads 20A, 20B may be separate leads, or bifurcated segments on a single lead. Some example configurations may comprise only a single lead. Two leads support bilateral stimulation in both brain hemispheres while one lead supports unilateral stimulation in one hemisphere.

Using the techniques described in this disclosure, a subset of electrodes 24, 26 of leads 20A and 20B, respectively, may be used to deliver electrical stimulation to patient 12 in order to reduce or eliminate oscillating signals within brain 28. As mentioned above, brain LFP and EEG rhythms may be associated with pathologies in various neurological and psychological disorders. As such, it may be desirable to reduce or eliminate these brain rhythms by delivering electrical stimulation with parameters and timing determined from a previously generated phase response map.

In one example, an oscillating signal of a brain, or brain rhythm, of a patient associated with a disorder may be measured and then a set of first electrical stimulation, (i.e., one or more test stimulation pulse(s), pulse trains, or continuous waveforms), may be delivered to the patient at some phase, or time, relative to a phase of the ongoing oscillating signal. The phase of the ongoing oscillating signal may be determined using a phase reference point such as the peak, trough, half rise time of an LFP, or similar rhythmic signal The response in the oscillating signal to a first electrical stimulation may be measured and then recorded and stored in memory, or the like. Another first electrical stimulation at another phase relative to the ongoing oscillating signal may then be delivered to the patient, and the response in the oscillating signal to the first electrical stimulation may be measured and then recorded. The process of delivering first electrical stimulation at different phases relative to the ongoing oscillation in the brain of the patient (e.g., sweeping through different phases, phase delays in a systematic, step-wise manner) and recording the responses in the oscillating signal to those different phases may be repeated. In this manner, a set of first electrical stimulation is delivered at a plurality of phases relative to the ongoing oscillating signal. Then, a phase at which to deliver second electrical stimulation, i.e., therapeutic electrical stimulation pulses, pulse trains, or continuous waveforms, based on the measured responses may be determined, and the second electrical stimulation therapy may be delivered to the patient at the determined phase.

In one example, each measured response in the oscillating signal may be mapped to the corresponding first electrical stimulation that caused the response and stored in a memory device. The mapping may be stored in memory in lookup tables, linked lists, hash tables, trees, binary trees, or any other type of data structure, for future reference and/or future therapy programming.

In some examples, a phase transition region such as the transition from phase delay to phase advance or similar critical phase region, such as a specific time or phase within the cycle, may be determined from the mapping, or phase response map. The phase(s) within these transition regions may be used as one or more times, relative to the ongoing oscillation, at which to deliver subsequent electrical stimulation relative to the ongoing oscillating signal. For example, a first group of phases, e.g., zero degrees through 85 degrees, at which electrical stimulation is delivered relative to an ongoing oscillating signal may cause an advance in phase of the oscillating signal. A second group of phases, e.g., 95 degrees through 180 degrees, at which electrical stimulation is delivered relative to the ongoing oscillating signal may cause a delay in phase of the oscillating signal. The one or more phases between the first group of phases (the "delay" group) and the second group of phases (the "advance" group) may correspond to a transition region between the delay and the advance of the phases of the oscillating signal. The phase of a subsequent beneficial electrical stimulation, i.e., therapeutic electrical stimulation, may, in some examples, be determined from one or more phases within the transition region, e.g., 86 degrees to 94 degrees. Subsequent delivery of possible therapeutic stimulation at specific phases can then be used to assess a therapeutic phase response map.

Continuing the example above, the second electrical stimulation may be determined to have a phase of 90 degrees, a value within the transition region between the advance and the delay of the phases of the oscillating signal. Once the phase of the second electrical stimulation is determined, e.g., 90 degrees, the second electrical stimulation may be delivered to the patient at the determined phase. It should be noted that the determined phase need not be a phase within the transition region. Rather, the determined phase at which second electrical stimulation is delivered may be a phase that produces an advance in the oscillating signal or a phase that produces a delay in the oscillating signal.

In some examples, the phases at which the first electrical stimulation, i.e., the test phases for generating the phase response map, is delivered may be increased or decreased from a starting phase in either a linear or non-linear manner. For example, it may be desirable to begin delivering the first electrical stimulation, i.e., the test electrical stimulation used to generate a phase response map, at a phase of five degrees relative to the ongoing oscillation, measure the response, increase the phase by five degrees, measure the response, and so on, in a linear manner. Or, in another example, it may be desirable to begin delivering the first electrical stimulation at a phase of five degrees relative to the ongoing oscillation, measure the response, increase the phase by ten degrees, measure the response, increase the phase by twenty degrees, and so on in a non-linear manner. In other examples, it may be desirable to deliver first electrical stimulation at a plurality of particular phases that correspond to "cross-over" points, i.e., angles at which an oscillating signal crosses an x-axis in a plot of the oscillating signal. Cross-over points may include angles such as 45 degrees, 90 degrees, 135 degrees, and 180 degrees. After delivery of the first electrical stimulation at one or more of cross-over points, a response to the first electrical stimulation at each cross-over point may be measured. It should be noted that it may be desirable to include a "quiet period," between successive delivery of first test electrical stimulation pulses (or waveforms), i.e., a period during which no electrical stimulation is delivered. A quiet period may allow the previously stimulated tissue time to recover, thereby ensuring that the response to a subsequent test pulse (or waveform) applied is independent of the response to an initial test pulse (or waveform). An example range of a quiet period may be about 1 cycle to about 20 cycles, or about 5 cycles to about 15 cycles, or about 8 cycles to about 12 cycles. The duration of the required quiet period can be determined for a specific patient or brain oscillation by characterizing a phase response curve map to a second test pulse and measuring the duration of time following an initial test stimulus for a stable phase response curve map to redevelop, or by waiting for stable brain oscillation amplitude or frequency to develop. In other examples, the phases at which the first electrical stimulation, i.e., the test phases for generating the phase response map, is delivered may generated in a pseudo-random manner. For example, the phases at which the first electrical stimulation is delivered may be randomly generated between certain ranges, e.g., between 0 degrees and 45 degrees, between 0 degrees and 30 degrees, or the like. In this manner, the range of phases may be constrained, but the selection of phases within the range may be random.

In another example, after the phase of the second electrical stimulation is determined from the measured responses to the set of first electrical stimulation (e.g., a first set of test electrical stimulation), an amplitude (current or voltage) of the second electrical stimulation may be determined. That is, if adjusting the phase of the first electrical stimulation has reduced but not eliminated the oscillating signal, increasing or decreasing an amplitude of a second set of first electrical stimulation (e.g., a second set of test electrical stimulation) may further reduce or eliminate the oscillating signal. In some examples, the amplitudes (current or voltage) at which the second set of first electrical stimulation is delivered may be increased or decreased from a starting amplitude in either a linear or non-linear manner. For example, a voltage amplitude of the first electrical stimulation may begin at about 0.1 volts (V) and be increased linearly or non-linearly through a plurality of amplitudes to about 15 V, with a response in the oscillating signal to each corresponding amplitude measured and stored. An amplitude that most reduces or eliminates the oscillating signal may be determined from the measured responses. Then, second electrical stimulation with the previously determined phase and amplitude may be delivered to the patient.

Continuing the example above, after determining that electrical stimulation therapy, i.e., second electrical stimulation, at a phase of 90 degrees relative to the ongoing oscillating signal should be delivered to the patient in order to reduce or eliminate the oscillating signal, a current amplitude (for systems utilizing current-controlled stimulation) or voltage amplitude (for systems utilizing voltage-controlled stimulation) may be determined. For example, it may be determined from the measured responses to the second set of first electrical stimulation (e.g., a second set of test electrical stimulation) that a voltage amplitude of 5 V essentially eliminates an oscillating signal in the brain of the patient. Thus, it may be desirable to deliver second electrical stimulation, i.e., electrical stimulation therapy, having an amplitude of 5 V at a phase of 90 degrees relative to the ongoing oscillating signal in order to provide efficacious electrical stimulation therapy for the treatment of one or more of chronic pain, tremor, Parkinson's disease, Alzheimer's disease, depression, epilepsy, migraines, as well as other movement disorders or neurodegenerative impairment.

Figure 2:
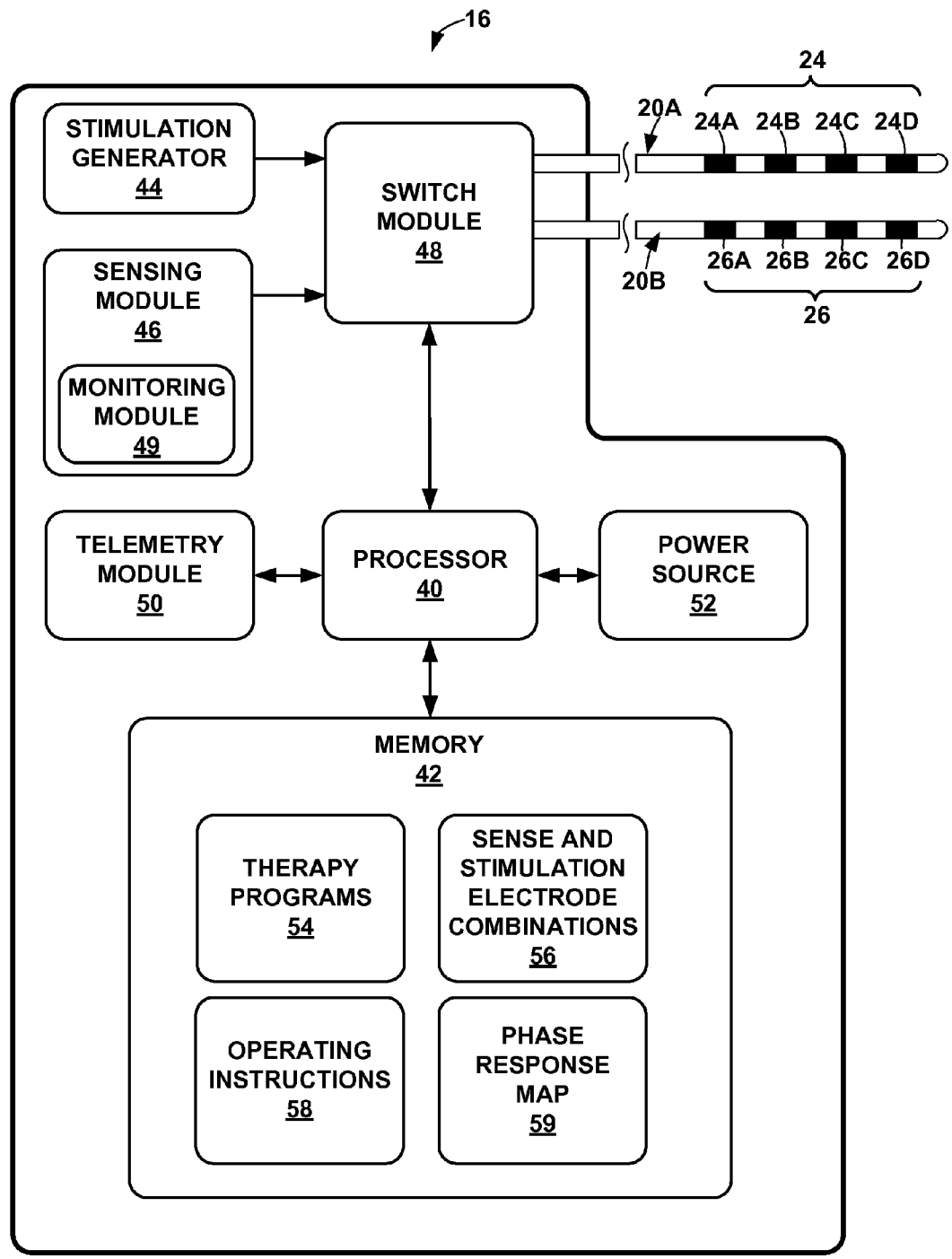
FIG. 2 is functional block diagram illustrating components of an example medical device that may be used to implement the techniques of this disclosure.

FIG. 2 is a functional block diagram illustrating components of an example medical device that may be used to implement the techniques of this disclosure. FIG. 2 is a functional block diagram illustrating components of an example IMD 16. In the example shown in FIG. 2, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

In the example shown in FIG. 2, memory 42 stores therapy programs 54, sense electrode combinations and associated stimulation electrode combinations 56, and operating instructions 58 in separate memories within memory 42. Each stored therapy program 54 defines a particular program of therapy in terms of respective values for electrical stimulation parameters, such as a stimulation electrode combination, electrode polarity, current or voltage amplitude, pulse width, and pulse rate. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 56 in memory 42 stores sense electrode combinations and associated stimulation electrode combinations. As described above, in some examples, the sense and stimulation electrode combinations may include the same subset of electrodes 24, 26, or may include different subsets of electrodes. Operating instructions 58 guide general operation of IMD 16 under control of processor 40, and may include instructions for measuring the impedance of electrodes 24, 26, for example. Processor 40 may map and store the measured responses, e.g., phases and amplitudes, of the oscillating signal to the delivered first electrical stimulation as phase response map 59, as will be discussed in more detail below.

Stimulation generator 44, under the control of processor 40, generates stimulation signals for delivery to patient 12 via selected combinations of electrodes 24, 26. An example range of electrical stimulation parameters believed to be effective in DBS to manage a movement disorder of patient include the following:

1. Frequency: between approximately 20 hertz (Hz) and approximately 500 Hz, such as approximately 130 Hz.

2. Voltage Amplitude: between approximately 0.1 volts and approximately 15 volts, such as between approximately 0.5 volts and approximately 10 volts, or approximately 5 volts.

3. Current Amplitude: A current amplitude may be defined as the biological load in which the voltage is delivered. In a current-controlled system, the current amplitude, assuming a lower level impedance of approximately 500 ohms, may be between approximately 0.2 milliamps to approximately 100 milliamps, such as between approximately 1 milliamps and approximately 40 milliamps, or approximately 10 milliamps. However, in some examples, the impedance may range between about 200 ohms and about 2 kili-ohms.

4. Pulse Width: between approximately 10 microseconds and approximately 5000 microseconds, such as between approximately 100 microseconds and approximately 1000 microseconds, or between approximately 180 microseconds and approximately 450 microseconds. The pulse width may generally correspond to less than about 45 degrees of an entire 360 degree cycle of the ongoing oscillating signal, but in some examples may be about 180 degrees.

5. Phase: The phase or timing of single therapeutic electrical stimulation pulses may be determined from the phase response map for the oscillating system. The phases of therapeutic stimulus delivery are generally those phases that produce large phase delays of the system or those phases near the phases that transition from phase delay to phase advance. Based upon subsequent delivery of therapeutic pulses or pulse trains and the beneficial responses to this stimulation, such as reduced amplitude of the unwanted oscillation or complete abolition of the oscillation, or observable clinical benefit, such as reduction of unwanted behaviors, similar critical phases of the oscillation can be determined.

6. Pulse Trains: A pulse train may be comprised of multiple single stimulation pulses separated from one another by a time referred to as an "interpulse interval." The interpulse interval is the time from the trailing edge of one pulse to the leading edge of the next pulse. The width of the entire pulse train (i.e., the time from the rising edge of the first pulse to the trailing edge of the last pulse, including all interpulse intervals) may generally correspond to less than about 45 degrees of an entire 360 degree cycle of the ongoing oscillating signal, but in some examples may be about 180 degrees.

7. Continuous waveforms: In addition to single pulses and pulse trains, continuous waveforms may be used to generate a phase response map in accordance with the disclosure. For example, a set of first electrical stimulation in the form of sinusoidal waveforms may be used to generate a phase response map. Generally, the duration of the continuous waveform should be less than the duration of the ongoing oscillating signal.

Stimulation generator 60 may, for example, generate either constant current-based or constant voltage-based stimulation in the form of pulses, pulse trains, or continuous waveforms. In delivering constant current-based stimulation, stimulation generator 60 maintains the amplitude of the current at a constant level. In delivering constant voltage-based stimulation, stimulation generator 60 maintains the amplitude of the voltage at a constant level.

Accordingly, in some examples, stimulation generator 44 generates electrical stimulation signals in accordance with the electrical stimulation parameters noted above. Other ranges of therapy parameter values may also be useful, and may depend on the target stimulation site within patient 12, which may be within brain 28 or other portions of the nervous system. While stimulation pulses are described, stimulation signals may be of any form, such as pulse trains, continuous-time signals (e.g., sine waves) or the like.

Processor 40 may include any one or more of a microprocessor, a controller, a digital signal processor (DSP), an application specific integrated circuit (ASIC), a field-programmable gate array (FPGA), discrete logic circuitry, and the functions attributed to processor 40 in this disclosure may be embodied as firmware, hardware, software or any combination thereof. Processor 40 controls stimulation generator 44 according to therapy programs 52 stored in memory 42 to deliver, or apply, particular stimulation parameter values specified by one or more of programs, such as amplitude, pulse width, and pulse rate.

In the example shown in FIG. 2, the set of electrodes 24 includes electrodes 24A, 24B, 24C, and 24D, and the set of electrodes 26 includes electrodes 26A, 26B, 26C, and 26D. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48.

Stimulation generator 44 may be a single channel or multichannel stimulation generator. In particular, stimulation generator 44 may be capable of delivering a single stimulation pulse, multiple stimulation pulses or continuous signal at a given time via a single electrode combination, or multiple stimulation pulses or continuous signals at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12. Or, in other examples, stimulation generator 44 may generate different stimulation parameters for different time slots.

Sensing module 46, under the control of processor 40, may sense bioelectrical brain signals and provide the sensed bioelectrical brain signals to processor 40. Processor 40 may control switch module 48 to couple sensing module 46 to selected combinations of electrodes 24, 26, i.e., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signals sensed across the selected electrodes 24, 26 to sensing module 46. The bioelectrical brain signals may include oscillating signals indicative of electrical activity within brain 28 of patient 12 and, in particular, electrical activity within one or more frequency bands, e.g., gamma frequency band (about 30 Hz and about 90 Hz), beta frequency band (about 12 Hz and about 30 Hz), delta frequency band (about 0.5 Hz and about 4 Hz), alpha frequency band (about 8 Hz and about 12 Hz), theta frequency band (about 4 Hz and about 8 Hz), and other frequency bands, of brain 28.

Although sensing module 46 is incorporated into a common housing with stimulation generator 44 and processor 40 in FIG. 2, in other examples, sensing module 46 may be in a separate housing from IMD 16 and may communicate with processor 40 via wired or wireless communication techniques. Example bioelectrical brain signals include, but are not limited to, a signal generated from local field potentials within one or more regions of brain 28. EEG and ECoG signals are examples of local field potentials (LFPs) that may be measured from brain 28. However, local field potentials may include a broader genus of electrical signals within brain 28 of patient 12.

As mentioned above, first electrical stimulation, i.e., test electrical stimulation used to generate the phase response map, may be delivered to an oscillating system at random phases or specific phases relative to the ongoing oscillation, and the phase of each test pulse relative to an ongoing oscillating signal in the oscillating system may be determined. In order to determine the phase of each test pulse relative to the ongoing oscillating signal, processor 40 may analyze bioelectrical brain signals within brain 28 of patient 12. For example, sensing module 46 may sense via a subset of electrodes 24, 26 (or a different subset of electrodes) bioelectrical brain signals of brain 28 and provide the sensed bioelectrical brain signals to processor 40. Upon receiving the sensed bioelectrical brain signals, processor 40 may analyze the received signals with respect to the delivered test pulses to determine the phase of each test pulse relative to the ongoing oscillating signal. Processor 40 may determine the phase of the ongoing oscillating signal using a phase reference point such as a peak, a trough, or a half rise time of an LFP or similar rhythmic signal. It should be noted that, in some example implementations, processor 60 (FIG. 3) of programmer 14 (or a computer) may analyze the bioelectrical brain signals of patient 12 and then transmit the analysis via telemetry module 64 to telemetry module 50 of IMD 16.

Sensing module 46 may include frequency monitoring module 49 capable of monitoring bioelectrical brain signals associated with patient 12 in selected frequency bands, e.g., gamma frequency band, beta frequency band, delta frequency band, alpha frequency band, theta frequency band, and other frequency bands of brain 28. Frequency monitoring module 49 may include tunable filtering and amplification capabilities that filter the bioelectrical brain signals into one or more signals and amplify the resulting filtered signal for analysis by processor 40. That is, frequency monitoring module 49 may be tuned, either by a clinician, patient, or without user intervention (i.e., automatically), to detect bioelectrical brain signals. Example circuitry capable of filtering and amplifying bioelectrical brain signals is described in U.S. patent application Ser. No. 12/237,868 to Denison et al., entitled, "FREQUENCY SELECTIVE MONITORING OF PHYSIOLOGICAL SIGNALS," which was filed on Sep. 25, 2008.

In accordance with the techniques of this disclosure, processor 40 controls stimulation generator 44 to deliver a set of first electrical stimulation, i.e., test electrical stimulation pulses, pulse trains, and continuous waveforms, used to generate a phase response map, at a plurality of different phases relative to the sensed ongoing oscillating bioelectrical brain signal in the patient. Based on the sensed ongoing oscillating signal, processor 40 may control stimulation generator 44 to deliver a set of first electrical stimulation according to programs stored as therapy programs 54 in memory 42, or according to programs transmitted to IMD 16 via programmer 14 (discussed in detail below). Therapy programs 54 may store, for example, a set of first electrical stimulation parameters such as current or voltage amplitudes, a starting phase at which first electrical stimulation should be delivered, an ending phase at which first electrical stimulation should be delivered, as well as step sizes that indicate the amount in degrees (or time) between successive phases of the first electrical stimulation, e.g., five degrees. If the step sizes are non-linear, as described above, therapy programs 54 may also include information that may be required to generate the plurality of phases, e.g., equations that define the non-linear relationship between the phases of the first electrical stimulation. Therapy programs 54 may also include parameters such as a duration of a first electrical stimulation pulse, pulse train, or continuous waveform as well as the frequency at which first electrical stimulation is delivered by stimulation generator 44.

After stimulation generator 44 delivers a first electrical stimulation pulse (or pulse train or waveform) to the patient, processor 40 may analyze the oscillating signal within brain 28 of patient 12, in the manner described above, to determine a phase response. Processor 40 stores in phase response map 59 of memory 42 the first electrical stimulation parameters, e.g., phase and amplitude of the pulse (or waveform) used to generate the first electrical stimulation pulse, and the phase and amplitude of the ongoing oscillating signal in the patient. For example, if stimulation generator 44 delivered a first electrical stimulation pulse having an amplitude of 50 μV and a phase of 30 degrees relative to the ongoing signal, and the ongoing oscillating signal advanced in phase by five degrees with no change in its amplitude, processor 40 would store these values as a first entry in phase response map 59 of memory 42.

After waiting a sufficient number of cycles to allow the stimulated tissue to recover, i.e., a quiet period, stimulation generator 44 delivers another first electrical stimulation pulse, i.e., another test pulse used to generate the phase response map, and processor 40 analyzes the oscillating signal within brain 28 of patient 12 to determine a phase response to this particular first electrical stimulation pulse. Processor 40 then stores the first electrical stimulation parameters associated with this particular stimulation pulse along with the phase response of the ongoing oscillating signal.

For example, if stimulation generator 44 delivered a first electrical stimulation pulse having an amplitude of 50 μV and a phase of 60 degrees relative to the ongoing signal, and the ongoing oscillating signal delayed in phase by five degrees with no change in its amplitude, processor 40 stores these values as a second entry in phase response map 59 of memory 42. After again waiting for a quiet period to end, stimulation generator 44 delivers another first electrical stimulation pulse and processor 40 analyzes the oscillating signal within brain 28 of patient 12 to determine a phase response to this particular first electrical stimulation pulse. For example, if stimulation generator 44 delivered a first electrical stimulation pulse having an amplitude of 50 μV and a phase of 90 degrees relative to the ongoing signal, and the ongoing oscillating signal neither advanced nor delayed in phase with no change in its amplitude, processor 40 stores these values as a third entry in phase response map 59 of memory 42. In this manner, a set of first electrical stimulation is delivered at a plurality of phases relative to the ongoing oscillating signal.

It should be noted that the ongoing oscillating signal may not respond (e.g., advance or delay) to any of the pulses, pulse trains, or waveforms delivered by stimulation generator 44 at any of the plurality of different phases relative to the ongoing signal delivered at a particular amplitude. For example, in the examples above, the ongoing signal may not respond to any of the first electrical stimulation pulses delivered with an amplitude of 50 μV. If processor 40 analyzes the oscillating signals within brain 28 of patient 12 and determines that there has been no phase response to these particular first electrical stimulation pulses delivered with an amplitude of 50 μV, then, in some examples, processor 40 may retrieve another therapy program 54 of memory 42 and control stimulation generator 44 to deliver first electrical stimulation with a different set of current or voltage amplitudes, for example. In the manner described above, processor 40 controls stimulation generator 44 to deliver first electrical stimulation, e.g., test electrical stimulation pulses, pulse trains, and continuous waveforms, using the new current or voltage amplitudes in order to generate a phase response map, at a plurality of different phases relative to the sensed ongoing oscillating bioelectrical brain signal in the patient. Processor 40 may need to adjust the current or voltage amplitudes one or more times in order to create first electrical stimulation that causes a response in the ongoing oscillating signal.

In addition to determining the change in phase and/or change in amplitude of the ongoing oscillating signal, processor 40 may measure a response to the first electrical stimulation by analyzing the ongoing oscillating signal to determine a change in the period of the ongoing oscillating signal. For example, processor 40 may determine whether the period, i.e., the duration of one cycle of the ongoing oscillating signal, has increased, decreased, or not changed.

After stimulation generator 44 generates and delivers the first electrical stimulation pulses (or waveforms), e.g., as determined by therapy programs 54, and after processor 40 stores the measured responses of the ongoing oscillating signal to each of the first electrical stimulation pulses, processor 40 analyzes the resulting phase response map 59 and determines a phase at which to deliver second electrical stimulation. In other words, processor 40 determines a phase at which to deliver second electrical stimulation based on the measured responses, e.g., a delay, an advance, or no change in a phase of the oscillating signal, a change in amplitude, a change in period, and a change in a phase response map, stored as phase response map 59. In some examples, processor 40 may periodically re-create phase response map 59 in order to calibrate the stimulation to account for possible changes over time.

As mentioned above, therapy programs 54 may also include parameters such as a duration of a first electrical stimulation pulse, pulse train, or continuous waveform as well as the frequency at which first electrical stimulation is delivered by stimulation generator 44. In some examples, stimulation generator 44 also generates and delivers the first electrical stimulation pulses (or waveforms) at a plurality of different stimulation durations, e.g., 1 millisecond, 2 milliseconds, 3 milliseconds, and/or at a plurality of different frequencies. Processor 40 may then analyze the oscillating signal within brain 28 of patient 12 after each of the different stimulation durations and/or different frequencies in order to determine a phase response. In this manner, multiple phase response maps may be generated and second electrical stimulation, i.e., therapeutic electrical stimulation pulses, pulse trains, or continuous waveforms, may be delivered to produce a therapeutic effect based on the phase response maps.

In some examples, processor 40 may analyze phase response map 59 and determine a transition region. A transition region, as described above, is one or more phases between a first group of phases that advance (or delay) the ongoing oscillating signal and a second group of phases that delay (or advance) the ongoing oscillating signal. In the example above, a first electrical stimulation pulse having a phase of 30 degrees relative to the ongoing oscillating signal advanced the ongoing oscillating signal by five degrees, and a first electrical stimulation pulse having a phase of 60 degrees relative to the ongoing oscillating signal delayed the ongoing oscillating signal by five degrees. Based on this information stored in phase response map 59, processor 40 may determine that a transition region exists between 30 degrees and 60 degrees. In the absence of additional data to fine tune the analysis (in this simple example, only three data points were stored in phase response map 59), processor 40 determines that electrical stimulation should be delivered at a phase of 45 degrees, a value between the endpoints of the transition region, in order to reduce or eliminate the ongoing oscillating signal. Then, stimulation generator 44 delivers the second electrical stimulation, i.e., the electrical stimulation therapy, to the patient at the determined phase, i.e., 45 degrees.

In some examples, it may be desirable to speed up the oscillating signal. As such, rather than selecting a phase within the transition region as described above, processor 40 may determine a phase within the advance region at which electrical stimulation should be delivered in order to speed up the oscillating signal. Or, it may be desirable to slow down the oscillating signal. As such, rather than selecting a phase within the advance region, processor 40 may determine a phase within the delay region at which electrical stimulation should be delivered in order to slow down the oscillating signal.

In some examples, as mentioned above, if the determined phase, e.g., 45 degrees, of the first electrical stimulation has reduced but not eliminated the oscillating signal, processor 40 may then increase or decrease an amplitude of the first electrical stimulation in an attempt to further reduce or eliminate the oscillating signal. In other words, after the phase of the second electrical stimulation is determined from the measured responses to the first electrical stimulation, processor 40 may determine an amplitude (current or voltage) of the second electrical stimulation. In some examples, processor 40 may increase or decrease the amplitudes (current or voltage) at which the first electrical stimulation is delivered from a starting amplitude in either a linear or non-linear manner. For example, stimulation generator 44 may deliver first electrical stimulation with a voltage amplitude beginning at about 0.1 V and increase the amplitude linearly or non-linearly through a plurality of amplitudes to about 15V. Processor 40 stores a response, e.g., an amplitude and a phase shift, of the oscillating signal to each corresponding amplitude in phase response map 59. Processor 40 then determines from the measured responses, i.e., phase response map 59, an amplitude that most reduces or eliminates the oscillating signal. Then, stimulation generator 44 delivers second electrical stimulation with the previously determined phase and amplitude to the patient.

In some examples, the system and, in particular, processor 40 may continue to measure the response of the oscillating signal to the second electrical stimulation at the determined phase. Processor 40 may monitor whether the second electrical stimulation continues to provide efficacious therapy or whether it may be desirable to generate another phase response map to determine another phase at which to deliver second electrical stimulation. In this manner, the system may employ closed-loop techniques for reducing or eliminating an ongoing oscillating signal.

Using the techniques of this disclosure, the system delivers a set of test pulses (or pulse trains or waveforms) with each test pulse having a phase relative to an ongoing oscillating signal in a patient's brain, measures a response in the oscillating signal to each of the plurality of test pulses, and generates a phase response map that may be used to deliver electrical stimulation therapy, i.e., second electrical stimulation, to the patient. The techniques described in this disclosure may be performed by a system that has already been implanted in a patient and programmed. The techniques may also be performed in clinical settings in which a system is being implanted in a patient and programming is being turned on for the first time. In a clinical implant setting, a clinician may also monitor the motor performance (e.g. clinical UPDRS, or similar clinical measure) of a patient as the first electrical stimulation is delivered. By monitoring the motor performance of patient 12 in response to receiving the electrical stimulation, a clinician may determine efficacious electrical stimulation settings that may be programmed into memory 42, including the phase and amplitude at which therapeutic electrical stimulation should be delivered. The determined stimulation settings may be programmed into memory 42 as part of therapy programs 54 for later use.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combinations, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
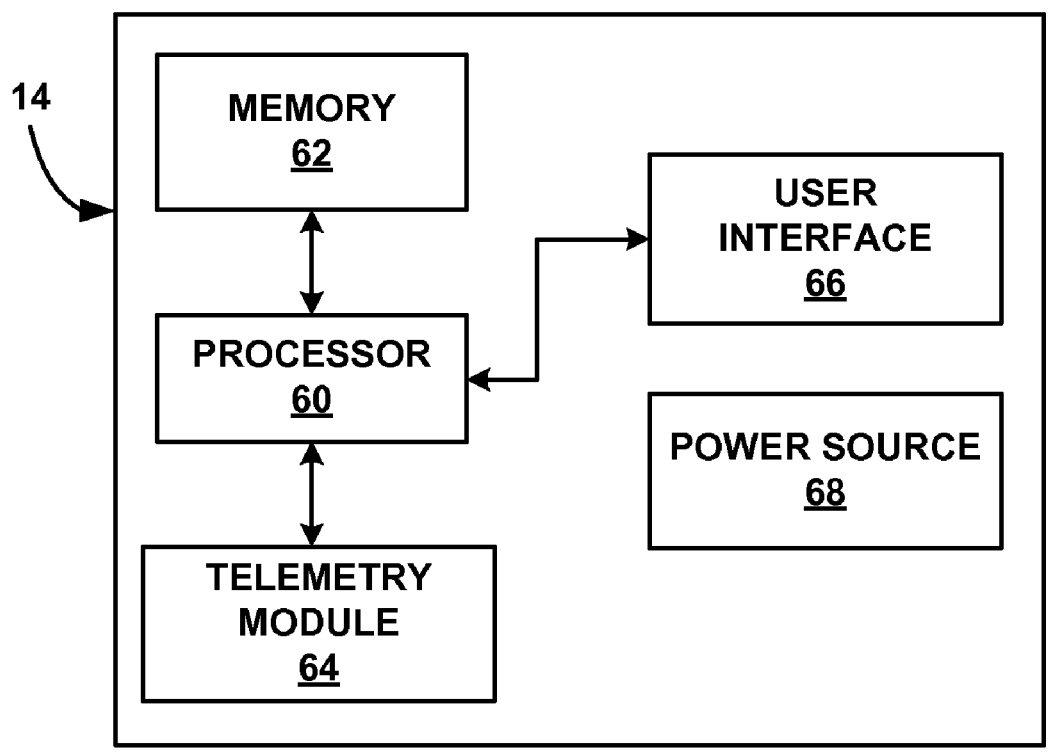
FIG. 3 is a functional block diagram illustrating components of an example medical device programmer that may be used to implement the techniques of this disclosure.

FIG. 3 is a functional block diagram illustrating components of an example medical device programmer that may be used to implement the techniques of this disclosure. Example external medical device programmer 14 of FIG. 3 includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 14 through user interface 66. User interface 66 includes a display (not shown), such as a LCD or LED display or other type of screen, to present information related to the therapy, such as information related to bioelectrical signals sensed via a plurality of sense electrode combinations. In addition, user interface 66 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 60 of programmer 14 and provide input.

If programmer 14 includes buttons and a keypad, the buttons may be dedicated to performing a certain function, e.g., a power button, or the buttons and the keypad may be soft keys that change in function depending upon the section of the user interface currently viewed by the user. Alternatively, the display (not shown) of programmer 14 may be a touch screen that allows the user to provide input directly to the user interface shown on the display. The user may use a finger, stylus, or other pointing medium to provide input to the display. In other examples, user interface 66 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 60 of programmer 14. For example, in some examples, processor 60 may receive a bioelectrical brain signal from IMD 16 or from a sensing module that is separate from IMD 16. The separate sensing module may, but need not be, implanted within patient 12. In some examples, processor 60 may analyze one or more bioelectrical brain signals sensed with the one or more sense electrode combinations associated with at least one of the stimulation electrode combinations. Based on the analysis of the bioelectrical brain signals, processor 60 may determine a frequency of an ongoing oscillating signal, generate a phase response map in a manner similar to that described above, and determine a phase (and, in some examples, an amplitude) at which second electrical stimulation should be delivered to the patient in order to reduce or eliminate the ongoing oscillating signal. In some cases, processor 60 may transmit a signal to IMD 16 to instruct IMD 16 to deliver second electrical stimulation, or alter delivery of second electrical stimulation by selecting a new program or switching stimulation electrode combinations.

Processor 40 of IMD 16 may receive the signal from programmer 14 via its respective telemetry module 50 (FIG. 3). Processor 40 of IMD 16 may deliver second electrical stimulation by selecting a stored therapy program from memory 42 based on the signal from processor 60 of programmer 14. Alternatively, processor 60 of programmer 14 may select a therapy program or a specific stimulation electrode combination and transmit a signal to IMD 16, where the signal indicates the therapy parameter values to be implemented by IMD 16 to help improve the efficacy of the stimulation to manage the patient's movement disorder. The indication may be, for example, an alphanumeric identifier or symbol that is associated with the therapy program in memory 42 of IMD 16.

Memory 62 may include instructions for operating user interface 66 and telemetry module 64, and for managing power source 68. Memory 62 may also store any therapy data retrieved from IMD 16 during the course of therapy. The clinician may use this therapy data to determine the progression of the patient condition in order to predict future treatment. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 delivers operating power to the components of programmer 14. Power source 68 may include a battery and a power generation circuit to produce the operating power. In some examples, the battery (e.g., nickel cadmium or lithium ion batteries) may be rechargeable to allow extended operation. Recharging may be accomplished by electrically coupling power source 68 to a cradle or plug that is connected to an alternating current (AC) outlet. In addition, recharging may be accomplished through proximal inductive interaction between an external charger and an inductive charging coil within programmer 14. In other examples, traditional batteries may be used. In addition, programmer 14 may be directly coupled to an alternating current outlet to operate. Power source 68 may include circuitry to monitor power remaining within a battery. In this manner, user interface 66 may provide a current battery level indicator or low battery level indicator when the battery needs to be replaced or recharged. In some cases, power source 68 may be capable of estimating the remaining time of operation using the current battery.

Figure 4A:
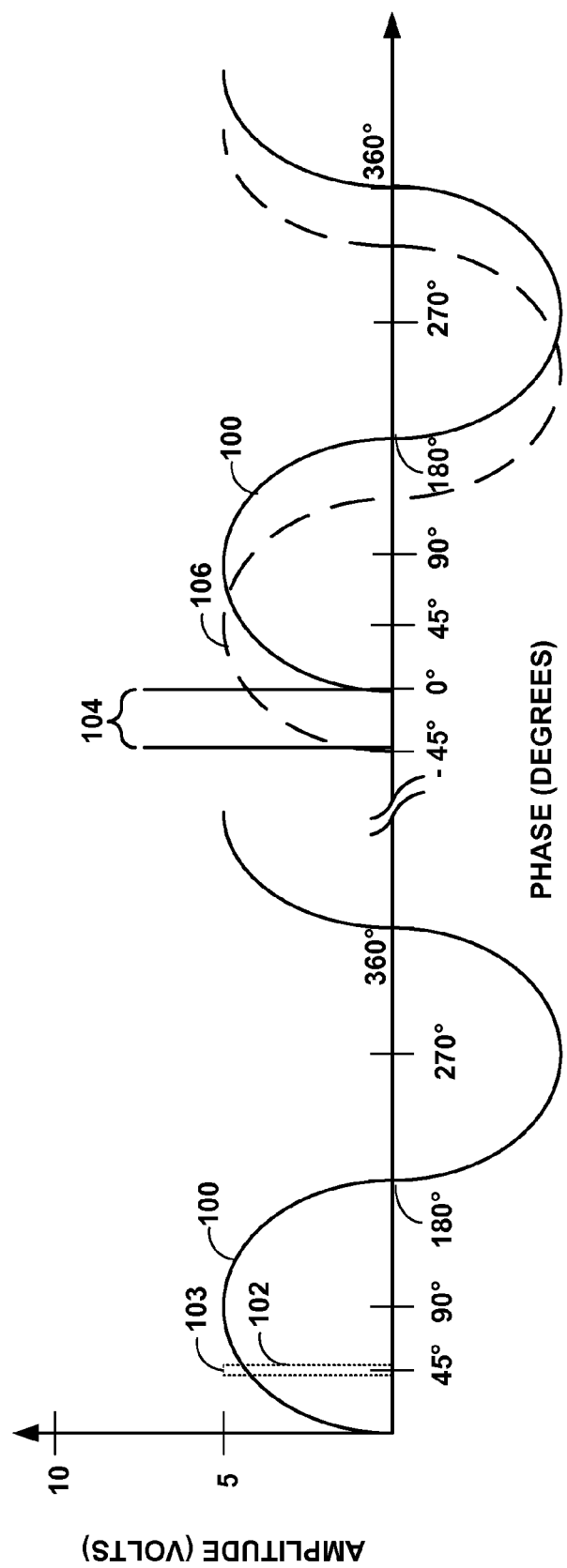
FIGS. 4A-4B are conceptual diagrams illustrating an example oscillating signal and its response to delivered electrical stimulation.
Figure 4B:
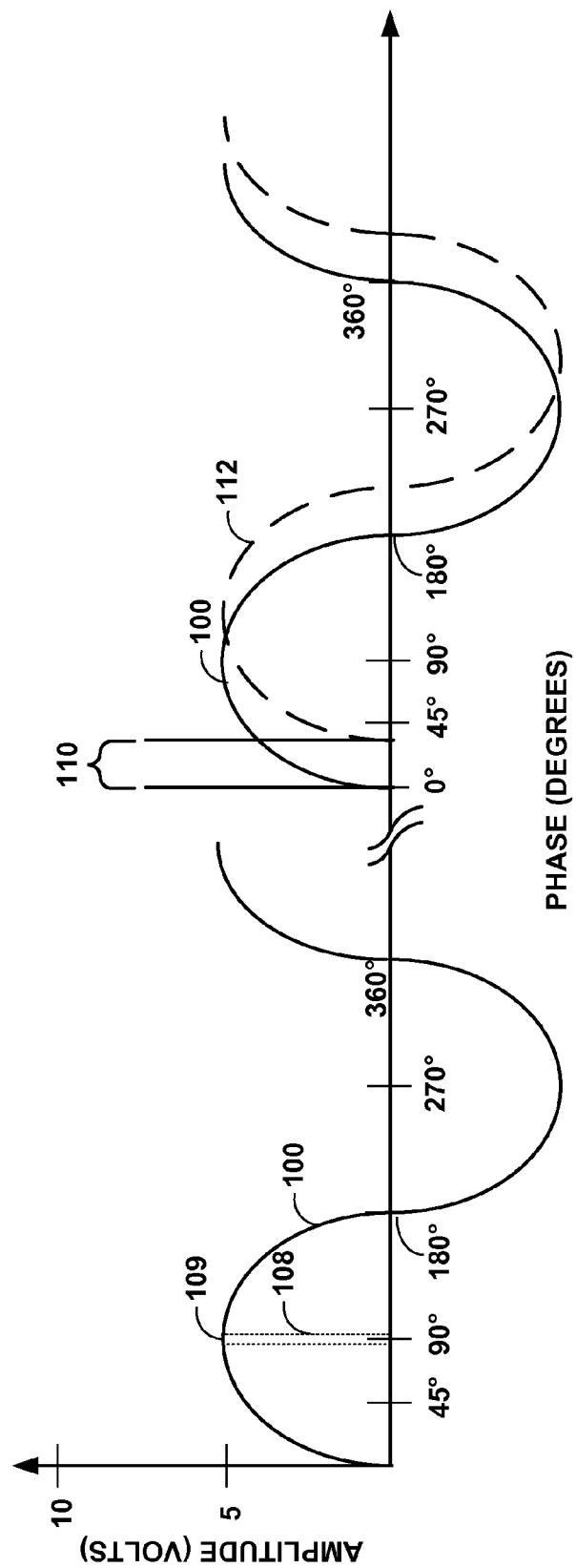

FIGS. 4A-4B are conceptual diagrams illustrating an example oscillating signal and its response to delivered electrical stimulation. FIG. 4A, left panel, graphically depicts ongoing oscillating signal 100 (solid line) in the brain of patient 6, as measured by sensing module 46 under the control of processor 40, along with first electrical stimulation pulse 102 (dotted line) applied by stimulation generator 44 of IMD 16. The y-axis of FIG. 4A represents the amplitude (in volts) of ongoing oscillating signal 100 and first electrical stimulation waveform 102. As seen in FIG. 4A, both ongoing oscillating signal 100 and first electrical stimulation pulse 102 have an amplitude of about 5 V. The x-axis of FIG. 4A represents the phase (in degrees) of first electrical stimulation pulse 102 in relation to ongoing oscillating signal 100. In FIG. 4A stimulation generator 44 delivers first electrical stimulation pulse 102 at a phase of about 45 degrees relative to ongoing oscillating signal 100. Although the pulse width of first electrical stimulation may generally correspond to less than about 45 degrees of an entire 360 degree cycle of the ongoing oscillating signal, in some examples, the pulse width may correspond to about 180 degrees. As seen in FIG. 4A, the pulse width 103 of first electrical stimulation pulse 102 corresponds to less than 10 degrees.

FIG. 4A, right panel, depicts the response of ongoing oscillating signal 100 to first electrical stimulation pulse 102. First electrical stimulation pulse 102 of FIG. 4A is applied at 45 degrees relative to ongoing oscillating signal 100 during the first cycle (i.e., first 360 degrees) of oscillating signal 100. In response, ongoing oscillating signal 100 advances in another cycle by about 45 degrees, as shown at 104. Dashed line 106 represents ongoing oscillating signal 100 after it has advanced about 45 degrees (ongoing oscillating signal 100 would have crossed the x-axis at 0 degrees, but due to first stimulation pulse 102, dashed line 106 representing the advanced signal crosses at about −45 degrees). Processor 40 may determine the phase of the ongoing oscillating signal by using a phase reference point such as the peak, trough, half rise time of an LFP, or similar rhythmic signal. It should be noted that in some examples, the response (e.g., phase advance) may measured in the cycles subsequent to cycle during which first electrical stimulation pulse was applied. As described above, processor 40 determines the phase shift (if any), e.g., an advance of about 45 degrees, and stores that phase shift along with the parameters that describe first electrical stimulation waveform 102 as an entry in phase response map 59.

FIG. 4B, left panel, graphically depicts ongoing oscillating signal 100 (solid line) in the brain of patient 6, as measured by sensing module 46 under the control of processor 40, along with first electrical stimulation pulse 108 (dotted line) applied by stimulation generator 44 of IMD 16. The y-axis of FIG. 4B represents the amplitude (in volts) of ongoing oscillating signal 100 and first electrical stimulation pulse 108. As seen in FIG. 4B, both ongoing oscillating signal 100 and first electrical stimulation pulse 108 have an amplitude of about 5 V. The x-axis of FIG. 4B represents the phase (in degrees) of first electrical stimulation pulse 108 in relation to ongoing oscillating signal 100. In FIG. 4B stimulation generator 44 delivers first electrical stimulation pulse 108 at a phase of 90 degrees relative to ongoing oscillating signal 100.

FIG. 4B, right panel, depicts the response of ongoing oscillating signal 100 to first electrical stimulation pulse 108. First electrical stimulation pulse 108 of FIG. 4B is applied at 90 degrees relative to ongoing oscillating signal 100 during the first cycle (i.e., first 360 degrees) of oscillating signal 100. In response, ongoing oscillating signal 100 delays in another cycle by about 40 degrees, as shown at 110. In FIG. 4B, dashed line 112 represents ongoing oscillating signal 102 after it has been delayed about 40 degrees. As described above, processor 40 determines the phase shift, e.g., a delay of about 40 degrees, and stores that phase shift along with the parameters that describe first electrical stimulation waveform 108 as an entry in phase response map 59. In this manner, processor 40 continues to populate phase response map 59 with entries that include first electrical stimulation parameters and the phase response of an ongoing oscillating signal to the first electrical stimulation. As seen in FIG. 4B, the pulse width 109 of first electrical stimulation pulse 102 corresponds to less than 10 degrees.

Figure 5A:
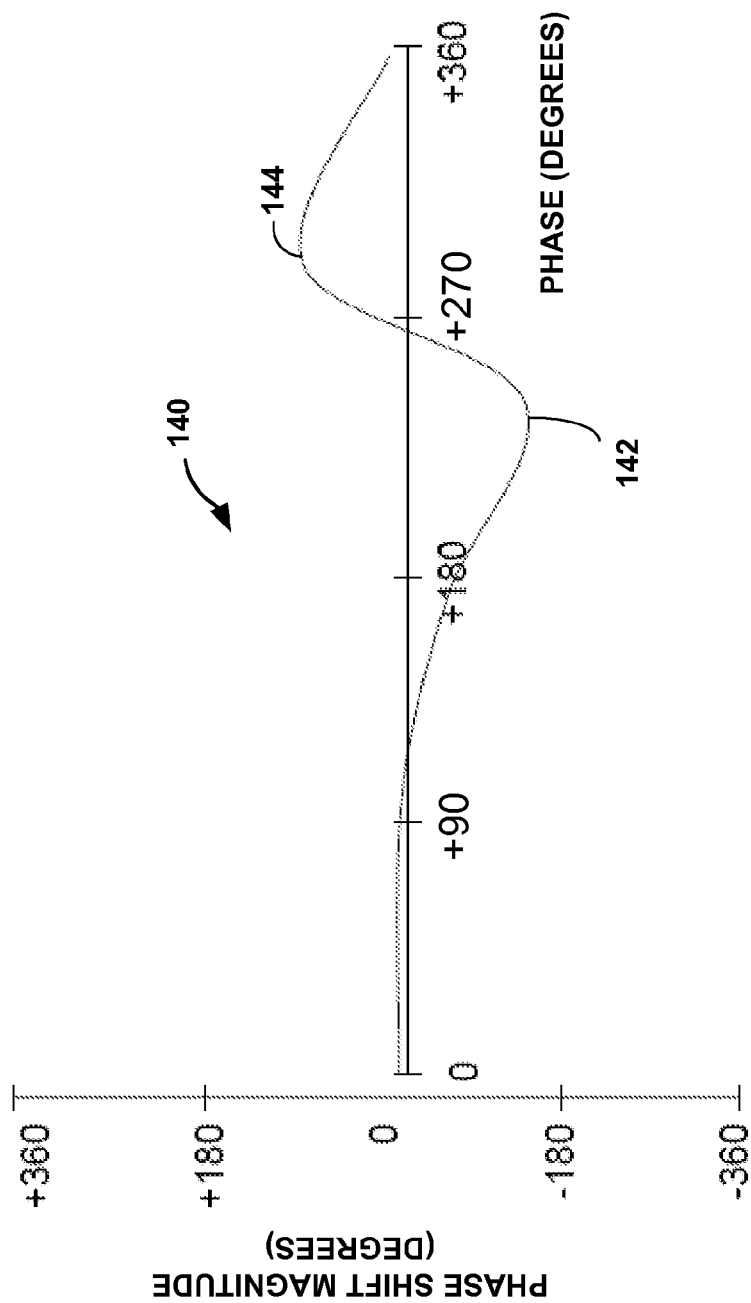
FIGS. 5A and 5B are conceptual diagrams illustrating example phase response maps.
Figure 5B:
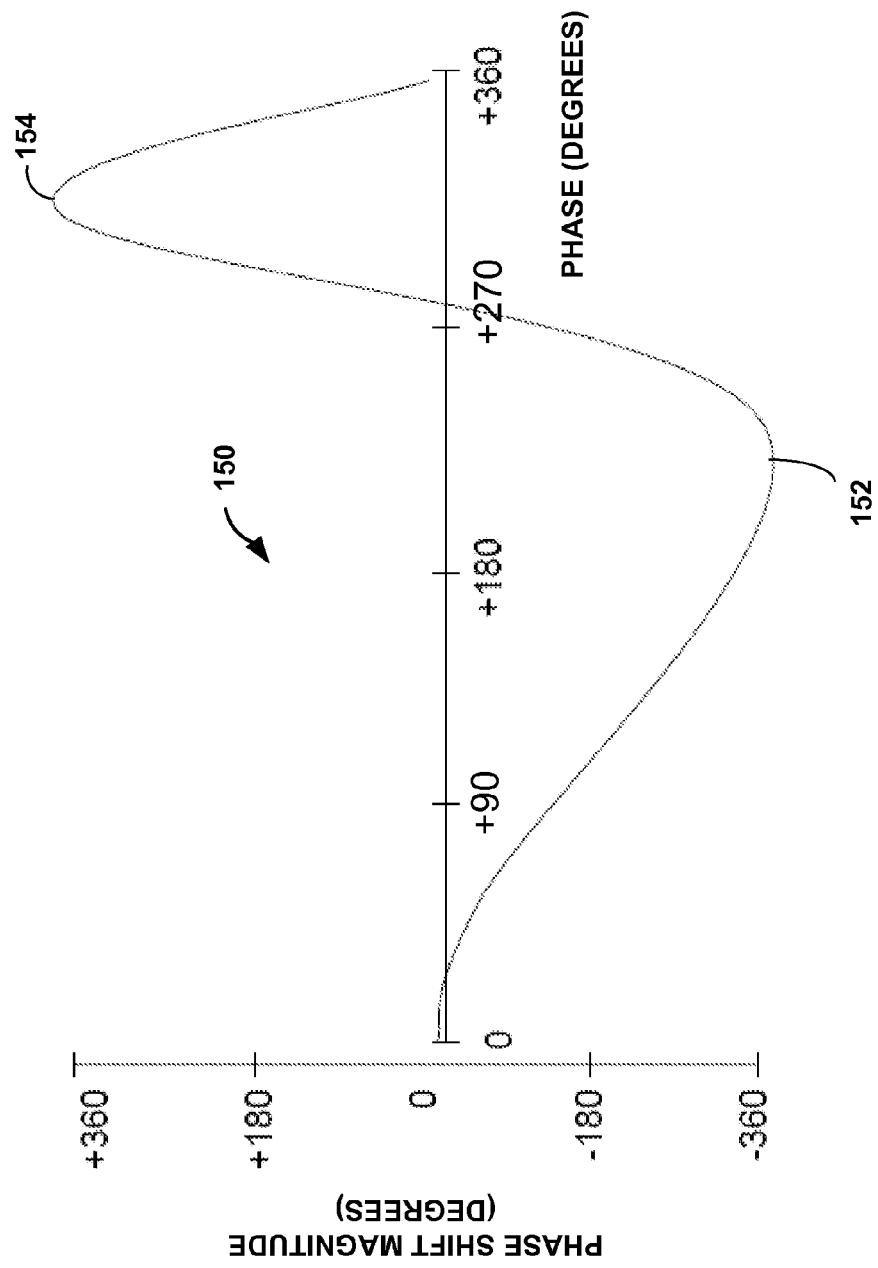

FIGS. 5A and 5B are conceptual diagrams illustrating example phase response maps. In FIGS. 5A and 5B, the y-axis represents the magnitude (in degrees) of the phase shift of the ongoing oscillation in response to the applied first electrical stimulation, i.e., test electrical stimulation. The x-axis represents the phase (in degrees) of the ongoing oscillating signal, e.g., ongoing oscillating signal 100 in FIGS. 4A and 4B.

FIG. 5A depicts phase response map 140. As seen in FIG. 5A, the phase shift in the ongoing oscillating signal is negligible until about 105 degrees. At about 250 degrees, the magnitude of the phase shift reaches about −150 degrees, as shown at 142. At about 315 degrees, the magnitude of the phase shift reaches about +90 degrees, as shown at 144.

FIG. 5B depicts phase response map 150 having a much larger response amplitude than phase response map 140. As seen in FIG. 5B, a phase shift in the ongoing oscillating signal begins at about 20 degrees relative to the ongoing oscillation, much sooner than in FIG. 5A. At about 225 degrees, the magnitude of the phase shift reaches about −360 degrees, as shown at 152. At about 315 degrees, the magnitude of the phase shift reaches about +360 degrees, as shown at 154.

Based on the response amplitude graphically depicted in phase response map 150, the ongoing oscillating signal was much more responsive to the first electrical stimulation, i.e., test electrical stimulation, that was delivered to generate phase response map 150 of FIG. 5B than the first electrical stimulation that was delivered to generate phase response map 140 of FIG. 5A. As such, processor 40 may select the first electrical stimulation parameters used to generate phase response map 150 of FIG. 5B for delivery of second electrical stimulation, i.e., therapeutic electrical stimulation pulses, pulse trains, or continuous waveforms.

As mentioned above, measuring a response to the set of first electrical stimulation may include one or more of measuring a phase, measuring a period, and measuring an amplitude of the oscillating signal after delivering the first electrical stimulation at each respective phase of the plurality of phases. In addition, changes in the phase response map itself may be used to measure a response of the ongoing oscillating signal to the set of first electrical stimulation. The phase response map is a characteristic of the oscillating signal and, as such, may also be used to determine the efficacy of the applied first electrical stimulation. For example, in FIG. 5B, there is a large amplitude response to the delivered first electrical stimulation at about 225 degrees (a phase shift magnitude of about −360 degrees, as shown at 152) and again at about 315 degrees (a phase shift magnitude of about +360 degrees, as shown at 154). Stimulation generator 44 may deliver substantially similar first electrical stimulation to the ongoing oscillating signal and processor 40 may analyze phase response map 150 to determine whether the phase response map changed. For example, if the phase shift remain unchanged, processor 40 may determine that the first electrical stimulation should be used for therapeutic purposes, i.e., for delivery of second electrical stimulation. If, however, the phase shift was much smaller despite the application of substantially similar first electrical stimulation, processor 40 may determine that the first electrical stimulation parameters should not be used for therapeutic purposes, given that the ongoing oscillating signals response to those first electrical stimulation parameters is not repeatable. For other therapeutic reasons, such as entraining the oscillation, choice of a particular stimulation may depend upon use of the smaller amplitude phase response map.

Figure 6:
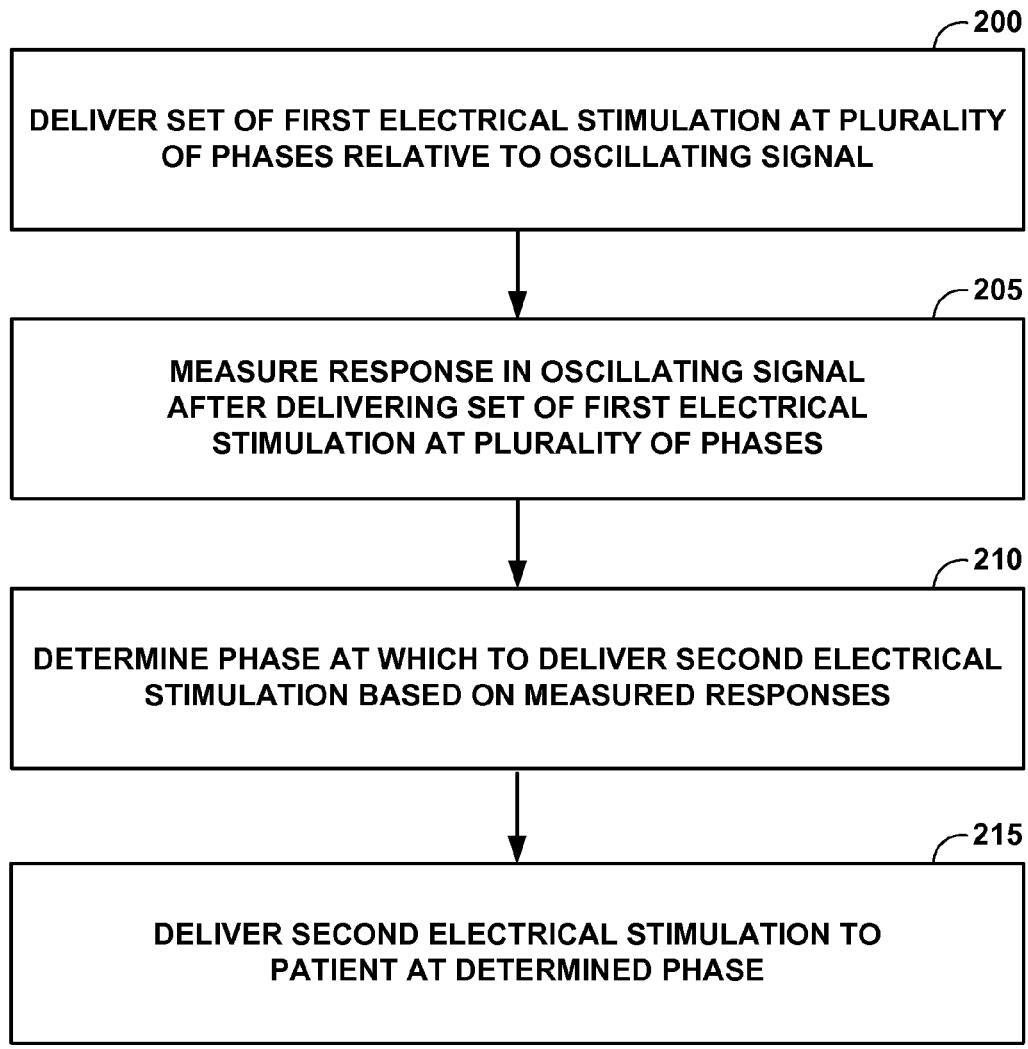
FIG. 6 is flow diagram illustrating an example method of delivering electrical stimulation using the techniques of this disclosure.

FIG. 6 is flow diagram illustrating an example method of delivering electrical stimulation using the techniques of this disclosure. In the example method shown in FIG. 6, IMD 16 and in particular, stimulation generator 44, delivers first electrical stimulation at a plurality of phases relative to an oscillating signal to the patient (200). After stimulation generator 44 delivers the first electrical stimulation at each respective phase of the plurality of phases, processor 40 measures a response in the oscillating signal to the first electrical stimulation (205), e.g., a delay, an advance, or no change in a phase of the oscillating signal, a change in amplitude, a change in period, and a change in a phase response map. Based on the measured responses, processor 40 determines a phase at which to deliver second electrical stimulation (210). For example, processor 40 may determine a phase from phase response map 59. Then, stimulation generator 44 delivers the second electrical stimulation to the patient at the determined phase (215).

In some examples, after determining a phase at which to deliver second electrical stimulation based on the measured response, processor 40 determines an amplitude of the second electrical stimulation and delivers the second electrical stimulation to the patient at the determined amplitude and phase. In other examples, the method in FIG. 6 includes processor 40 mapping each measured response in the oscillating signal to the corresponding first electrical stimulation and storing the mapping in a memory device, e.g., memory 42.

In some examples, processor 40 determines, from the mapping, a transition region between first electrical stimulation that causes a delay in a phase of the oscillating signal and first electrical stimulation that causes an advance in a phase of the oscillating signal, and stimulation generator 44 delivers the second electrical stimulation to the patient at a phase within the transition region and at a first amplitude.

In one example, processor 40 determines from the mapping, a transition region between first electrical stimulation that causes a delay in a phase of the oscillating signal and first electrical stimulation that causes an advance in a phase of the oscillating signal. Stimulation generator 44 delivers the first electrical stimulation to the patient at a phase within the transition region and at a plurality of stimulus amplitudes or stimulus durations. Processor 40 determines a phase and an amplitude at which to deliver second electrical stimulation based on the measured responses, and stimulation generator 44 delivering the second electrical stimulation to the patient at the determined phase and amplitude. Responses of the ongoing oscillation to these stimulations at a plurality of stimulation amplitudes and duration can be assessed and selected depending upon their effects on the oscillation as well as therapeutic outcome.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples of the disclosure have been described. These and other examples are within the scope of the following claims.

The invention claimed is:

1. A method comprising:
   delivering a set of first electrical stimulation at a plurality of phases relative to an oscillating signal;
   after delivering the set of first electrical stimulation at each respective phase of the plurality of phases, measuring a response in the oscillating signal to the set of first electrical stimulation;
   determining a phase at which to deliver second electrical stimulation based on the measured responses; and
   delivering the second electrical stimulation to the patient at the determined phase to produce a therapeutic effect.

2. The method of claim 1, wherein the set of first electrical stimulation is a first set of first electrical stimulation, the method further comprising:
   after determining a phase at which to deliver second electrical stimulation based on the measured response, delivering a second set of first electrical stimulation at the determined phase and at a plurality of amplitudes and durations;
   after delivering the second set of first electrical stimulation at the determined phase and at each respective amplitude of the plurality of amplitudes, measuring a response in the oscillating signal to the second set of first electrical stimulation;
   determining an amplitude of the second electrical stimulation based on the measured responses,
   wherein delivering second electrical stimulation to the patient at the determined phase further comprises delivering second electrical stimulation to the patient at the determined amplitude.

3. The method of claim 1, wherein measuring a response to the set of first electrical stimulation comprises one or more of measuring a change in a phase response map, measuring a phase, measuring a period, and measuring an amplitude of the oscillating signal after delivering the first electrical stimulation at each respective phase of the plurality of phases.

4. The method of claim 3, further comprising:
   mapping each measured response in the oscillating signal to the corresponding first electrical stimulation; and
   storing the mapping in a memory device.

5. The method of claim 4, wherein determining a phase at which to deliver second electrical stimulation based on the measured responses comprises:
   determining, from the mapping, a transition region between first electrical stimulation that causes a delay in a phase of the oscillating signal and first electrical stimulation that causes an advance in a phase of the oscillating signal; and
   delivering the second electrical stimulation to the patient at a phase within the transition region.

6. The method of claim 4, wherein determining a phase at which to deliver second electrical stimulation based on the measured responses comprises:
   determining, from the mapping, a transition region between first electrical stimulation that causes a delay in a phase of the oscillating signal and first electrical stimulation that causes an advance in a phase of the oscillating signal;
   delivering a second set of first electrical stimulation to the patient at the phase within the transition region and at a plurality of amplitudes;
   measuring a response in the oscillating signal to the second set of first electrical stimulation;
   determining a phase and an amplitude at which to deliver second electrical stimulation based on the measured responses; and
   delivering the second electrical stimulation to the patient at the determined phase and amplitude.

7. The method of claim 1, wherein the second electrical stimulation is configured to treat at least one of chronic pain, tremor, Parkinson's disease, depression, epilepsy, migraines, and Alzheimer's disease.

8. The method of claim 1, wherein delivering a set of first electrical stimulation at a plurality of phases relative to the oscillating signal to the patient comprises:
   delivering a set of first electrical stimulation at a plurality of phases relative to the oscillating signal to the patient in one of a linear manner or non-linear manner.

9. A device comprising:
   an implantable housing;
   one or more leads coupled to the housing;
   one or more electrodes carried by the one or more leads; and
   a processor configured to:
     control delivery of a set of first electrical stimulation at a plurality of phases relative to an oscillating signal;

after delivery of the set of first electrical stimulation at each respective phase of the plurality of phases, measure a response in the oscillating signal to the set of first electrical stimulation;

determine a phase at which to deliver second electrical stimulation based on the measured responses; and control delivery of the second electrical stimulation to the patient at the determined phase to produce a therapeutic effect.

10. The device of claim 9, wherein the set of first electrical stimulation is a first set of first electrical stimulation, the processor further configured to:

after determining a phase at which to deliver second electrical stimulation based on the measured response, control delivery of a second set of first electrical stimulation at the determined phase and at a plurality of amplitudes and durations;

after controlling delivery of the second set of first electrical stimulation at the determined phase and at each respective amplitude of the plurality of amplitudes, measure a response in the oscillating signal to the second set of first electrical stimulation;

determine an amplitude of the second electrical stimulation based on the measured responses, wherein controlling delivery of second electrical stimulation to the patient at the determined phase further comprises controlling delivery of second electrical stimulation to the patient at the determined amplitude.

11. The device of claim 9, wherein the processor configured to measure a response to the set of first electrical stimulation is further configured to one or more of measure a change in a phase response map, measure a phase, measure a period, and measure an amplitude of the oscillating signal after controlling delivery of the first electrical stimulation at each respective phase of the plurality of phases.

12. The device of claim 11, wherein the processor is further configured to:

map each measured response in the oscillating signal to the corresponding first electrical stimulation; and store the map in a memory device.

13. The device of claim 12, wherein the processor configured to determine a phase at which to deliver second electrical stimulation based on the measured responses is further configured to:

determine, from the map, a transition region between first electrical stimulation that causes a delay in a phase of the oscillating signal and first electrical stimulation that causes an advance in a phase of the oscillating signal; and control delivery of the second electrical stimulation to the patient at a phase within the transition region.

14. The device of claim 12, wherein the processor configured to determine a phase at which to deliver second electrical stimulation based on the measured responses is further configured to:

determine, from the map, a transition region between first electrical stimulation that causes a delay in a phase of the oscillating signal and first electrical stimulation that causes an advance in a phase of the oscillating signal;

control delivery of a second set of first electrical stimulation to the patient at the phase within the transition region and at a plurality of amplitudes;

measure a response in the oscillating signal to the second set of first electrical stimulation;

determine a phase and an amplitude at which to deliver second electrical stimulation based on the measured responses; and control delivery of the second electrical stimulation to the patient at the determined phase and amplitude.

15. The device of claim 9, wherein the second electrical stimulation is configured to treat at least one of chronic pain, tremor, Parkinson's disease, depression, epilepsy, migraines, and Alzheimer's disease.

16. The device of claim 9, wherein the processor configured to control delivery of a set of first electrical stimulation at a plurality of phases relative to the oscillating signal to the patient is further configured to:

control delivery of a set of first electrical stimulation at a plurality of phases relative to the oscillating signal to the patient in one of a linear manner or non-linear manner.

17. A computer-readable storage medium comprising instructions that, when executed by a processor, cause the processor to:

control delivery of a set of first electrical stimulation at a plurality of phases relative to an oscillating signal;

after delivery of the set of first electrical stimulation at each respective phase of the plurality of phases, measure a response in the oscillating signal to the set of first electrical stimulation;

determine a phase at which to deliver second electrical stimulation based on the measured responses; and control delivery of the second electrical stimulation to the patient at the determined phase to produce a therapeutic effect.

18. The computer-readable storage medium of claim 17, wherein the set of first electrical stimulation is a first set of first electrical stimulation, the computer-readable storage medium further comprising instructions that, when executed by the processor, cause the processor to:

after determining a phase at which to deliver second electrical stimulation based on the measured response, control delivery of a second set of first electrical stimulation at the determined phase and at a plurality of amplitudes and durations;

after delivering the second set of first electrical stimulation at the determined phase and at each respective amplitude of the plurality of amplitudes, measure a response in the oscillating signal to the second set of first electrical stimulation;

determine an amplitude of the second electrical stimulation based on the measured responses, wherein controlling delivery of second electrical stimulation to the patient at the determined phase further comprises controlling delivery of second electrical stimulation to the patient at the determined amplitude.

19. The computer-readable storage medium of claim 18, wherein the instructions that, when executed by the processor, cause the processor to measure a response to the set of first electrical stimulation comprise instructions that, when executed by the processor, cause the processor to one or more of measure a change in a phase response map, measure a phase, measuring a period, and measure an amplitude of the oscillating signal after delivering the first electrical stimulation at each respective phase of the plurality of phases.

20. The computer-readable storage medium of claim 19, further comprising instructions that, when executed by the processor, cause the processor to:

map each measured response in the oscillating signal to the corresponding first electrical stimulation; and store the map in a memory device.

21. The computer-readable storage medium of claim 20, wherein the instructions that, when executed by the processor, cause the processor to determine a phase at which to deliver second electrical stimulation based on the measured responses comprise instructions that, when executed by the processor, cause the processor to:

determine, from the map, a transition region between first electrical stimulation that causes a delay in a phase of the oscillating signal and first electrical stimulation that causes an advance in a phase of the oscillating signal; and control delivery of the second electrical stimulation to the patient at a phase within the transition region.

22. The computer-readable storage medium of claim 20, wherein the instructions that, when executed by the processor, cause the processor to determine a phase at which to deliver second electrical stimulation based on the measured responses comprise instructions that, when executed by the processor, cause the processor to:

determine, from the map, a transition region between first electrical stimulation that causes a delay in a phase of the oscillating signal and first electrical stimulation that causes an advance in a phase of the oscillating signal;

control delivery of a second set of first electrical stimulation to the patient at the phase within the transition region and at a plurality of amplitudes;

measure a response in the oscillating signal to the second set of first electrical stimulation;

determine a phase and an amplitude at which to deliver second electrical stimulation based on the measured responses; and control delivery of the second electrical stimulation to the patient at the determined phase and amplitude.

23. The computer-readable storage medium of claim 17, wherein the second electrical stimulation is configured to treat at least one of chronic pain, tremor, Parkinson's disease, depression, epilepsy, migraines, and Alzheimer's disease.

24. The computer-readable storage medium of claim 17, wherein the instructions that, when executed by the processor, cause the processor to control delivery of a set of first electrical stimulation at a plurality of phases relative to the oscillating signal to the patient comprises:

control delivery of a set of first electrical stimulation at a plurality of phases relative to the oscillating signal to the patient in one of a linear manner or non-linear manner.

25. A device comprising:

means for delivering a set of first electrical stimulation at a plurality of phases relative to an oscillating signal;

means for measuring a response in the oscillating signal to the set of first electrical stimulation after delivering the set of first electrical stimulation at each respective phase of the plurality of phases;

means for determining a phase at which to deliver second electrical stimulation based on the measured responses; and means for delivering the second electrical stimulation to the patient at the determined phase to produce a therapeutic effect.

* * * * *